(12) United States Patent
Yamasaki et al.

(10) Patent No.: US 9,987,210 B2
(45) Date of Patent: Jun. 5, 2018

(54) COSMETIC CONDITIONING OIL COMPOSITION AND COSMETIC PRODUCT

(71) Applicant: DOC Japan Co., Ltd., Tokyo (JP)

(72) Inventors: Emi Yamasaki, Tokyo (JP); Jianzhong Yang, Hyogo (JP)

(73) Assignee: DOC JAPAN CO., LTD., Tokyo (JP)

( * ) Notice: Subject to any disclaimer, the term of this patent is extended or adjusted under 35 U.S.C. 154(b) by 0 days. days.

(21) Appl. No.: 15/124,683

(22) PCT Filed: Mar. 11, 2014

(86) PCT No.: PCT/JP2014/001347
§ 371 (c)(1),
(2) Date: Sep. 9, 2016

(87) PCT Pub. No.: WO2015/136568
PCT Pub. Date: Sep. 17, 2015

(65) Prior Publication Data
US 2017/0014324 A1  Jan. 19, 2017

(51) Int. Cl.
| A61K 8/37 | (2006.01) |
| A61Q 5/02 | (2006.01) |
| A61Q 5/12 | (2006.01) |
| A61K 8/31 | (2006.01) |
| A61Q 19/00 | (2006.01) |
| A61K 8/81 | (2006.01) |
| A61K 8/86 | (2006.01) |
| A61Q 19/10 | (2006.01) |
| A61K 8/02 | (2006.01) |
| A61K 8/67 | (2006.01) |
| A61K 8/73 | (2006.01) |

(52) U.S. Cl.
CPC .............. *A61K 8/37* (2013.01); *A61K 8/0216* (2013.01); *A61K 8/31* (2013.01); *A61K 8/375* (2013.01); *A61K 8/673* (2013.01); *A61K 8/678* (2013.01); *A61K 8/73* (2013.01); *A61K 8/8111* (2013.01); *A61K 8/8117* (2013.01); *A61K 8/86* (2013.01); *A61Q 5/02* (2013.01); *A61Q 5/12* (2013.01); *A61Q 19/00* (2013.01); *A61Q 19/10* (2013.01); *A61K 2800/34* (2013.01); *A61K 2800/48* (2013.01)

(58) Field of Classification Search
None
See application file for complete search history.

(56) References Cited

U.S. PATENT DOCUMENTS

| 4,797,272 A * | 1/1989 | Linn ...................... A61K 8/064 424/59 |
| 2003/0113357 A1 * | 6/2003 | Bell ........................ A61K 8/345 424/401 |
| 2003/0143178 A1 | 7/2003 | Komure et al. |
| 2003/0157048 A1 | 8/2003 | Komure et al. |
| 2007/0166262 A1 | 7/2007 | Pratley et al. |
| 2009/0123398 A1 | 5/2009 | Laba et al. |
| 2010/0143426 A1 | 6/2010 | Laba et al. |
| 2011/0189248 A1 | 8/2011 | Baldaro et al. |
| 2012/0288458 A1 * | 11/2012 | Yamaguchi ............ A61K 8/064 424/60 |

FOREIGN PATENT DOCUMENTS

| JP | 61-286311 A | 12/1986 |
| JP | 2004-517812 A | 6/2004 |
| JP | 2007-153806 A | 6/2007 |
| JP | 2008162965 A | 7/2008 |
| JP | 2011-213630 A | 10/2011 |
| JP | 2011213621 A | 10/2011 |
| JP | 2013-023478 A | 2/2013 |
| JP | 2013053081 A | 3/2013 |
| JP | 2013227288 A | 11/2013 |
| JP | 2013249301 A | 12/2013 |
| JP | 2014009259 A | 1/2014 |
| WO | 2005/025526 A1 | 3/2005 |
| WO | 2006/003733 A1 | 1/2006 |
| WO | 2009/064790 A1 | 5/2009 |
| WO | 2010/068661 A1 | 6/2010 |

OTHER PUBLICATIONS

Fragrance Journal, vol. 36(7), Fragrance Journal Ltd, Jul. 15, 2008, p. 57.
Binks, Bernard P et al: "Dry oil powders and oil foams stabilised by fluorinated clay platelet particles", Soft Matter, vol. 10, No. 4, Dec. 9, 2013, pp. 578-589.
Korosi, Gabor et al: "Density and surface tension of 83 organic liquids", Journal of Chemical and Engineering Data., vol. 26, No. 3, Jul. 1, 1981, pp. 323-332.
Chumpitaz, Lucy D.A. et al: "Surface Tension of Fatty Acids and Triglycerides", Journal of the American Oil Chemists' Society, vol. 76, No. 3, Jan. 1, 1999, pp. 379-382.
European search report dated Sep. 18, 2017 for corresponding EP application EP14885373.2.
Regulation (EC) No. 1223/2009 of the European Parliament and of the Council of Nov. 30, 2009 on cosmetic products (recast) (Text with EEA relevance) (OJ L 342, Dec. 22, 2009, p. 59).
IFRA RIFM QRA Information Booklet Version 7.1 Revised Jul. 9, 2015.
Yuan, C. L. , et al.; "Study on characteristics and harm of surfactants"; Journal of Chemical and Pharmaceutical Research, 2014, 6(7): 2233-2237.
Acker, S., et al; "The Easy Way to Make a Sunscreen"; International Journal for Applied Science; SOFW Journal 140; Jul. 2014.
Lucas Meyer Cosmetics; "Suncare Solutions".
BASF; "UV Protection with Nothing to Hide".

*Primary Examiner* — Jennifer A Berrios
(74) *Attorney, Agent, or Firm* — Nath, Goldberg & Meyer; Joshua B. Goldberg; Tanya E. Harkins

(57) ABSTRACT

Disclosed is a cosmetic conditioning oil composition comprising of an oil or mixture of oils having surface tension in the range of 26 dyne/cm or lower and an oil thickener, wherein the composition has a viscosity about 5,000 cps or higher at 25 degrees Celsius. The composition of the present invention can provide improved conditioning benefits such as smoothness, softness, and ease of combing for hair when applied in shampoos, conditioner, treatments, and skin cleansing products as a silicone alternative.

1 Claim, No Drawings

COSMETIC CONDITIONING OIL COMPOSITION AND COSMETIC PRODUCT

This is a National Phase Application filed under 35 U.S.C. 371 as a national stage of international application no. PCT/JP2014/001347, filed Mar. 11, 2014, the content of which is hereby incorporated by reference in its entirety.

TECHNICAL FIELD

The present invention relates to a cosmetic conditioning oil composition and a cosmetic product.

BACKGROUND ART

Hair conditioning benefit can be delivered from rinse-off shampoo, conditioner, treatment, and leave-on conditioning products. Similarly, skin or scalp moisturizing benefit can be delivered from either rinse-off or leave-on products. Smoothening hair surface is the fundamental for hair conditioning, leading to consumer perception of ease of combing, soft and smooth feel, shine, manageable hair, stronger hair, etc. So far, silicones are the most widely applied hair smoothening or conditioning agent (See, PTL 1). Silicone can be also used to provide moisturizing benefit to skin. There are two characteristics for silicones responsible for their superior conditioning benefits, i.e. low surface tension and variety of viscosities. Typically, the surface tensions for silicones are between 16 dyne/cm to 24 dyne/cm. The viscosities of silicones can vary from about 5 cst to about 20,000,000 cst. The low surface tension makes silicone easily spread on hair or skin surface to form thin lubrication film. Sufficient viscosity helps silicone to survive rinsing to be able to deposit on hair or skin surface.

CITATION LIST

Patent Literature

PTL 1: JP 2013-023478

SUMMARY OF INVENTION

Technical Problem

Recently, there is an increasing trend for silicone-free hair care products. Consumers suspect that silicones may overly deposit and stimulate on their hair or scalp, causing negative hair or scalp feeling. In responding to this new situation, many hair care manufactures are now providing silicone-free shampoos, conditioners, and treatments to consumers. However, in many cases these silicone-free products do not deliver sufficient hair conditioning benefit.

Based on the foregoing, there remains a desire for non-silicone type of conditioning oils which provide superior surface smoothening and conditioning benefits similar to silicone.

None of the existing art provides all of the advantages and benefits of the present invention.

Solution to Problem

The present invention is directed to a cosmetic conditioning oil composition comprising by weight:

(A) from about 1% to about 99% of an oil or mixture of oils having surface tension in the range of 26 dyne/cm or lower;

(B) from about 0.01% to about 50% of an oil thickener;

wherein the composition has a viscosity about 5,000 cps or higher at 25 degrees Celsius.

Advantageous Effects of Invention

The composition of the present invention can provide improved cosmetic conditioning benefits, especially when applied in hair shampoos, conditioners, treatments or skin cleansing products as a silicone alternative. These and other features, aspects, and advantages of the present invention will become better understood from a reading of the following description, and appended claims.

DESCRIPTION OF EMBODIMENTS

While the specification concludes with claims particularly pointing out and distinctly claiming the invention, it is believed that the present invention will be better understood from the following description.

Herein, "comprising" means that other steps and other ingredients which do not affect the end result can be added. This term encompasses the terms "consisting of" and "consisting essentially of".

All percentages, parts and ratios are based upon the total weight of the compositions of the present invention, unless otherwise specified. All such weights as they pertain to listed ingredients are based on the active level and, therefore, do not include carriers or by-products that may be included in commercially available materials.

Herein, "mixture" is meant to include a simple combination of materials and any compounds that may result from their combination.

Compositions

The cosmetic conditioning oil composition of the present invention comprises an oil or mixture of oils; an oil thickener; wherein the oil or mixture of oils have surface tension in the range of 26 dyne/cm or lower; and wherein the composition has a viscosity from about 5,000 cps or higher at 25 degrees Celsius. For example, the cosmetic conditioning oil composition can include a hair or skin conditioning oil composition. It is believed that, by using the oils having a surface tension of 26 dyne/cm or lower, the composition of the present invention can readily form thin lubrication film on hair or skin surface to provide improved conditioning benefits. It is also believed that, by using the oil thickener to create a viscosity of 5,000 cps or higher at 25 degrees Celsius, the compositions can have sufficient resistant force to survive rinsing when applied in shampoos, conditioners, and other rinse-off hair care or skin care products. It is believed that, the conditioning oil composition comprising from about 1% to about 99% of an oil or mixture of oils having surface tension in the range of 26 dyne/em or lower; from about 0.01% to about 50% an oil thickener; wherein the composition has a viscosity about 5,000 cps or higher at 25 degrees Celsius, can provide improved conditioning benefits, especially when applied in cosmetic product (e.g., hair shampoos, conditioners, treatments or skin cleansing products) as a silicone alternative.

In view of providing the above oil composition, the oil and thickener are contained at a level such that the weight ratio of the oil to the thickener is in the range of about 1:1 to about 100:1, preferably from about 2:1 to about 99:1, more preferably from about 4:1 to about 49:1.

The cosmetic conditioning oil composition of the present invention has a viscosity about 5,000 cps or higher at 25 degrees Celsius, preferably about 7,500 cps or higher at 25 degrees Celsius, more preferably about 10,000 cps or higher at 25 degrees Celsius.

Oils

The compositions of the present invention comprise from about 1% to about 99% of an oil or mixture of oils. The oils useful herein are those having surface tension in the range of 26 dyne/cm or lower.

An oil is any natural or synthetic substance that is a liquid at ambient temperatures, and is in general hydrophobic and immiscible with water, although it can have both hydrophobic and lipophilic portions. An oil usually has a high carbon content in its molecule. Oils may be animal, plant, or petrolum in origin, and may be volatile or non-volatile. Some oils can be used as lubricant to reduce surface friction under the condition that the oils can cover the surface efficiently. The surface tension of water is about 72 dynes/cm at 25 degrees Celsius, while most of oils have a surface tension lower than that of water, typically between 16 dynes/cm to 45 dynes/cm at 25 degrees Celsius.

Oils in the present invention have a surface tension in the range of 26 dyne/cm or lower. Without intending to be limited by theory, it is believed that such oils tend to have an ability of forming thin occlusive lubrication film on hair surface, and thus delivering hair or skin conditioning benefits such as improved smoothness, combability, shininess, softness, and slipperiness.

Silicones or polydimethylsiloxanes are synthetic oils produced through polymerization. Silicones usually have a surface tension in the range of 16 dyne/cm to 24 dyne/cm. Depending on its polymerization degree, viscosities of silicones can vary from about 5 cst to about 20,000,000 cst. When applied in a rinse-off product such as shampoo, conditioner, or body soap, silicones or silicone mixtures having an overall viscosity of from about 5,000 cps or higher at 25 degrees Celsius are usually used.

Polyolefins such as poly-a-olefins are also polymeric oils, having a viscosity from about 6 cps to about 60,000 cps. However, surface tensions for polyolefins are higher than 28 dyne/cm. Therefore, while polyolefins can be deposited on hair or skin surface from a rinse-off product, conditioning effect of polyolefins are not superior due to the high surface tension.

Most of non-silicone types of oils have surface tensions higher than 26 dyne/cm. For example, surface tension of mineral oil is about 29.7 dyne/cm; surface tension of olive oil is about 32 dyne/cm; surface tension of paraffin is about 26.4 dyne/cm.

However, there are non-silicone and non-polymer type of oils that have a surface tension in the range of 26 dyne/cm or lower. These oils can be fluorine-containing oily compounds, hydrocarbons having branched or unsaturated structure, and ester oils having branched or unsaturated structure. Fluorine-containing oily compounds may have safety concern in personal application, and thus are not highly preferred. Preferred examples of the oil useful herein include hydrocarbons having branched or unsaturated structure, and ester oils having branched or unsaturated structure. Unless otherwise specifically noted, the oil or mixture of oils may be included at a level of from about 1% to about 99% by weight of the conditioning oil composition.

a. Ester Oil

Esters are chemical compounds consisting of a carbonyl adjacent to an ether linkage. An ester oil has one or more ester groups and alkyl groups connected with the ester groups. Each R is independently a $C_1$-$C_{22}$ alkyl. Each R may be either a straight or branched, a saturated or unsaturated alkyl chain. The ester oil typically has a melting point of less than about 40 degrees Celsius, and is preferably water-insoluble, and in a liquid form at 25 degrees Celsius.

The ester oils useful herein are those having a surface tension of 26 dyne/cm or lower. Particularly useful ester oils herein include cetyl ethylhexanoate with trade name EXEPARL HO available from Kao Chemical, tricaprylin with trade name of Myritol 880 available from Cognis, part of BASF, or trade name of COCONARD RK available from Kao Chemical, isononyl isononanoate with trade name of CETIOL ININ available from Cognis, part of BASF, and PPG-1 ceteth-3 acetate.

b. Hydrocarbon

Hydrocarbon oils include straight, cyclic, and branched hydrocarbons. The hydrocarbon can be either saturated or unsaturated, having a length from about 12 to about 40 carbon atoms. The hydrocarbon oil typically has a melting point of less than about 40 degrees Celsius, and is preferably water-insoluble, and in a liquid form at 25 degrees Celsius.

The hydrocarbon oils useful herein are those having a surface tension of 26 dyne/cm or lower. Particularly useful hydrocarbon oils herein include isohexadecane with trade name of Permethyl101A available from Presperse, squalane with trade name of Pripure 3759 available from Croda or trade name of NIKKOL squalane from Nikko Chemicals.

Oil Thickeners

Thickening agents, or thickeners, is the term applied to substances which increase the viscosity of a solution or a liquid without substantially modifying its other properties. When the liquid to be thickened is an oil, the thickener is namely an oil thickener. Oil thickeners are soluble in oil or miscible with oil, providing viscosity to the oil by forming a gel or dissolving in the oil phase as a colloid mixture that forms a weakly cohesive internal structure.

Particularly useful oil thickener herein include dextrin palmitate with trade name of Rheopearl KL available from Chiba Flour Milling or trade name of Rheopearl TL available from Chiba Flour Milling, dextrin palmitate/ethylhexanoate with trade name of Rheopearl TT available from Chiba Flour Milling, Glyceryl behenate, polyglyceryl-6 octastearate with trade name of Taiset 50-C available from Taiyo Kagaku, ethylene oxide-butylene oxide block copolymers with a trade name of WILBRIDE RC-9050 available from NOF, hydrogenated polydecene/hydrogenated styrene/isoprene copolymer/tocopherol with a trade name of PIONIER GEL 12 PAO available from Hansen & Rosenthal.

Unless otherwise specifically noted, the oil thickener may be included at a level of from about 0.01% to about 50% by weight of the conditioning oil composition.

Additional Components

The composition of the present invention may include other additional components, which may be selected according to the desired characteristics of the final composition and which are suitable for rendering the composition more cosmetically or aesthetically acceptable or to provide them with additional usage benefits. Such other additional components generally are used individually at levels of from about 0.001% to about 10%, preferably up to about 5% by weight of the composition.

A wide variety of other additional components can be formulated into the present compositions. These include: other hair conditioning oils such as oleyl erucate with a trade name of Cetiol J 600 available from Cognis, part of BASF, hydrogenated polyisobutene with a trade name of ParLeam available from NOF, PPG-3 caprylyl ether with a trade name of Sofcare GP-1 from Kao Chemical; scalp care ingredients such as vitamin E with tradename Emix-d available from Eisai, panthenol available from Roche, panthenyl ethyl ether available from Roche, plant extracts, and nutrients.

Method of Preparation

The cosmetic conditioning oil compositions as shown above can be prepared as follows: Oil is heated to 85-90 degrees Celsius. Oil thickener is then added and mixed into the oil with agitation. The mixture is maintained at a temperature of 85-90 degrees Celsius until the components are homogenized, and no solids are observed. When included, other additional components are added with agitation. The mixture is then slowly cooled to room temperature.

The mixtures obtained can be then added into hair care or skin care products such as shampoos and body soaps consisting of anionic surfactants for cleaning, cationic polymers for coacevation, water as a carrier, and optionally pearling agent; hair conditioners or treatments consisting of cationic surfactants, fatty alcohols, optionally humectants and thickening polymers, and water. The mixtures can be added directly or as a pre-emulsified emulsion using anionic, nonionic, or cationic surfactants as an emulsifier.

When applied in hair care or skin care products, the embodiments disclosed have many advantages. For example, they are especially suitable for replacing silicones in rinse-off hair care or skin care products, and can provide improved conditioning benefits such as smoothness, softness, and ease of combing for hair. When applied in hair care shampoos and conditioners, the embodiments disclosed deliver at least 10% of reduction on required combing force as measured by a combing tester compared to other non-silicone type of oils.

Examples

The following examples further describe and demonstrate embodiments within the scope of the present invention. The examples are given solely for the purpose of illustration and are not to be construed as limitations of the present invention, as many variations thereof are possible without departing from the spirit and scope of the invention. Where applicable, ingredients are identified by chemical or INCI name, or otherwise defined below.

All percentages are based upon the total weight of the compositions of the present invention, unless otherwise specified. All such weights as they pertain to listed ingredients are based on the active level and, therefore, do not include carriers or by-products that may be included in commercially available materials.

Each of the cosmetic conditioning oil compositions of "Ex. 1" through "Ex. 10" was prepared as follows: Oil was heated to 85-90 degrees Celsius. Oil thickener was then added and mixed into the oil with agitation. The mixture was maintained at a temperature of 85-90 degrees Celsius until the components were homogenized, and no solids were observed. When included, other additional components were added with agitation. The mixture was then slowly cooled to room temperature.

When applied in hair care shampoos and conditioners, "Ex. 1" through "Ex. 10" deliver at least 10% of reduction on required combing force as measured by a combing tester compared to other non-silicone type of oils.

Compositions (wt %)

TABLE 1

| type | Components | Ex. 1 | Ex. 2 | Ex. 3 | Ex. 4 | Ex. 5 |
|---|---|---|---|---|---|---|
| Ester oil | Cetyl ethylhexanoate*1 | 80 | | | | |
| | Tricapylin*2 | | 85 | | | |
| | PPG-1 ceteth-3 acetate | | | 80 | | |
| | Isononyl isononanoate*3 | | | | 90 | |
| hydrocarbon | Isohexadecane*4 | | | | | 90 |
| | Squalane*5 | | | | | |
| Oil thickener | Dextrin palmitate*6 | 10 | | | | |
| | Dextrin palmitate/ethylhexanoate*7 | | 10 | 5 | | |
| | Glyceryl behenate, polyglyceryl-6 octastearate*8 | | | 5 | | |
| | Ethylene oxide-butylene oxide block copolymers*9 | | | | 10 | |
| | Hydrogenated polydecene/hydrogenated styrene/isoprene copolymer/tocophero*10 | | | | | 10 |
| Additional component | Oleyl enicate*11 | 5 | 5 | | | |
| | Hydrogenated polyisobutene*12 | | 1 | 5 | | |
| | PPG-3 caprylyl ether*13 | 5 | 1 | 5 | | |
| | Vitamin E | | 1 | | | |
| | Panthenol | | 1 | | | |
| | Panthenyl ethyl ether | | 1 | | | |

TABLE 2

| | Components | Ex. 6 | Ex. 7 | Ex. 8 | Ex. 9 | Ex. 10 |
|---|---|---|---|---|---|---|
| Ester oil | Cetyl ethylhexanoate*1 | 90 | | | 50 | 15 |
| | Tricaprylin*2 | | 70 | | | 15 |
| | PPG-1 ceteth-3 acetate | | | | | 15 |
| | Isononyl isononanoate*3 | | | | | |
| hydrocarbon | Isohexadecane*4 | | | | 30 | 15 |
| | Squalane*5 | | | 90 | | 15 |
| Oil thickener | Dextrin palmitate*6 | | | 10 | 5 | |
| | Dextrin palmitate/ethylhexanoate*7 | 9 | | | 5 | |
| | Glyceryl behenate, polyglyceryl-6 octastcarate*8 | | 5 | | | |

TABLE 2-continued

| | Components | Ex. 6 | Ex. 7 | Ex. 8 | Ex. 9 | Ex. 10 |
|---|---|---|---|---|---|---|
| Additional component | Ethylene oxide-butylene oxide block copolymers*9 | | | 5 | | 10 |
| | Hydrogenated polydecene/hydrogenated styrene/isoprene copolymer/tocophero*10 | | | | | |
| | Oleyl erucate*11 | | 5 | | 5 | |
| | Hydrogenated polyisobutene*12 | | 5 | | | |
| | PPG-3 caprylyl ether*13 | | | 5 | 5 | |
| | Vitamin E | 0.5 | | | | 5 |
| | Panthenol | 0.25 | | | | 1 |
| | Panthenyl ethyl ether | 0.25 | | | | 1 |

Definitions of Components

1 Cetyl ethylhexanoate: EXEPARL HO available from Kao Chemical.

2 Tricaprylin: Myritol 880 available from Cognis, part of BASF; or COCONARD RK available from Kao Chemical.

3 Isononyl isononanoate: CETIOL ININ available from Cognis, part of BASF.

4 Isohexadecane: Permethyl101A available from Presperse.

5 Squalane: Pripure 3759 available from Croda; or NIKKOL squalane from Nikko Chemicals.

6 Dextrin palmitate: Rheopearl KL available from Chiba Flour Milling; or Rheopearl TL available from Chiba Flour Milling.

7 Dextrin palmitate/ethylhexanoate: Rheopearl TT available from Chiba Flour Milling.

8 Glyceryl behenate, polyglyceryl-6 octastearate: Taiset 50-C available from Taiyo Kagaku.

9 Ethylene oxide-butylene oxide block copolymers: WILBRIDE RC-9050 available from NOF.

10 Hydrogenated polydecene/hydrogenated styrene/isoprene copolymer/tocopherol: PIONIER GEL 12 PAO available from Hansen & Rosenthal.

11 Oleyl erucate: Cetiol J 600 available from Cognis, part of BASF.

12 Hydrogenated polyisobutene: ParLeam available from NOF.

13 PPG-3 caprylyl ether: Sofcare GP-1 from Kao Chemical.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

The invention claimed is:

1. A cosmetic conditioning oil composition consisting of:
 (A) from about 1% to about 99% by weight of an oil having surface tension in the range of 26 dyne/cm or lower which is cetyl ethylhexanoate;
 (B) from about 0.01% to about 50% by weight of an oil thickener which is dextrin palmitate; and
 (C) from about 0.001% to about 10% by weight of at least one additional component selected from the group consisting of oleyl erucate, hydrogenated polyisobutene, PPG-3 caprylyl ether, vitamin E, panthenol, panthenyl ethyl ether, plant extracts, and nutrients;
 wherein a weight ratio of cetyl ethylhexanoate to dextrin palmitate is in the range of about 4:1 to about 49:1,
 wherein the composition has a viscosity of 5,000 cps or higher at 25° C., and
 wherein the composition is in the form of gel.

* * * * *